United States Patent
Yoo

(10) Patent No.: US 7,362,426 B1
(45) Date of Patent: Apr. 22, 2008

(54) RAMAN AND PHOTOLUMINESCENCE SPECTROSCOPY

(75) Inventor: Woo Sik Yoo, Palo Alto, CA (US)

(73) Assignee: WaferMasters, Inc., San Jose, CA (US)

( * ) Notice: Subject to any disclaimer, the term of this patent is extended or adjusted under 35 U.S.C. 154(b) by 0 days.

(21) Appl. No.: 11/539,426

(22) Filed: Oct. 6, 2006

(51) Int. Cl.
*G01N 21/64* (2006.01)
*G01N 21/65* (2006.01)

(52) U.S. Cl. .................. 356/73; 356/301; 356/318
(58) Field of Classification Search .............. 356/72, 356/73, 301
See application file for complete search history.

(56) References Cited

U.S. PATENT DOCUMENTS

2002/0109110 A1 * 8/2002 Some et al. ............. 250/559.4

OTHER PUBLICATIONS

A. Singha, "A non-destructive analytic tool for nanostructured materials: Raman and photoluminescence spectroscopy", arXir:cond-mat/0406096, v1, Jun. 4, 2004 (pp. 1-32).

* cited by examiner

*Primary Examiner*—F. L. Evans
(74) *Attorney, Agent, or Firm*—MacPherson Kwok Chen & Heid LLP; Tom Chen

(57) ABSTRACT

Systems and techniques for contemporaneous Raman and photoluminescence spectroscopy. Light that has interacted with a sample is dispersed to separate wavelength components, including Raman and photoluminescence components. A first array detector is positioned to receive Raman components, and a second array detector is positioned to receive Raman components. The first array detector and the second array detector may comprise the same detector material, or different detector materials.

20 Claims, 12 Drawing Sheets

RAMAN AND PHOTOLUMINESCENCE SPECTROSCOPY

TECHNICAL FIELD

This invention generally relates to spectroscopy.

BACKGROUND

Understanding the properties of materials is important in many applications. Spectroscopic techniques can be used to obtain important information about materials, particularly at or near the material surface.

One spectroscopy technique is Raman spectroscopy, based on the Raman effect. The Raman effect occurs as a result of molecular deformations in electric field E, determined by molecular polarisability a. A laser beam can be considered an oscillating electromagnetic wave with electrical vector E. Upon interaction with the sample, it induces an electric dipole moment P=a*E, which deforms molecules. Periodically deformed molecules begin vibrating with characteristic frequency $v_m$. The amplitude of vibration is known as nuclear displacement. In other words, monochromatic laser light with frequency $v_0$ excites molecules and transforms them into oscillating dipoles.

Another spectroscopy technique is photoluminescence (sometimes referred to herein as "PL"). Photoluminescence is the optical emission obtained by photon excitation, typically using a laser. The energy from photons of the excitation light source excite electrons of the material from lower energy states to higher energy states. The electrons subsequently return to the lower energy state, each emitting a photon with a frequency proportional to the difference in energy between the high energy and low energy states. Photoluminescence techniques can be used for non-destructive characterization of materials, such as semiconductors. One common use of photoluminescence spectroscopy is to determine material composition, since different materials emit photons of different wavelengths, depending on the particular transition generating the photon.

SUMMARY

Systems and techniques described herein provide for efficient and high quality spectroscopy. Both Raman and photoluminescence spectra may be obtained during a single scan of a sample using array detectors positioned and configured to receive the Raman and photoluminescence wavelength components of light that has interacted with a sample.

In general, in one aspect, a spectroscopy system comprises an aperture (an optical input port to the spectroscopy system) positioned to receive light from a sample, the light including a plurality of wavelength components including photoluminescence wavelength components and Raman shifted components. The system may further include a dispersion element positioned in the optical path of the light and configured to spatially disperse the wavelength components of the light. The system may further include a first array detector positioned to receive Raman shifted components and to generate one or more signals indicative of intensity of the Raman shifted components and a second array detector positioned to receive photoluminescence components and to generate one or more signals indicative of intensity of the photoluminescence components.

The system may include a curved mirror positioned to receive the light from the aperture and to reflect the light to the dispersion element. The system may further comprise a mirror positioned to receive light from the dispersion element and to reflect the light to the first array detector and the second detector.

The system may comprise a first mirror positioned to receive light from the dispersion element and to reflect the light to the first array detector, and a second mirror positioned to receive light from the dispersion element and to reflect the light to the second array detector. The first array detector comprises a first detector material, and the second array detector may comprise the same material or a second different detector material. The first detector material may comprise silicon, and the second different detector material comprises a material with a bandgap larger than one electron volt.

The system may be configured to perform time-resolved Raman and PL spectroscopy. The system may comprise at least one of an optical chopper and a pulsed laser to intermittently transmit light to the sample.

The system may be configured to probe a sample with a plurality of excitation wavelengths. The system may comprise a light source configured to generate light of a plurality of wavelengths to intermittently or constantly transmit light to the sample.

The system may comprise a stage configured to position the sample with respect to incoming excitation light. The system may comprise the sample positioned on the stage.

In general, in another aspect, a spectroscopy system may comprise a first aperture positioned to receive light from a region of a sample at a particular time, the light including a plurality of wavelength components including Raman wavelength components. The system may comprise a second aperture positioned to receive light from the region of the sample at the particular time, the light including a plurality of wavelength components including photoluminescence shifted components. The system may include a first dispersion element positioned in the optical path of the light received through the first aperture and configured to spatially disperse the Raman wavelength components of the light received through the first aperture. The system may comprise a second dispersion element positioned in the optical path of the light received through the second aperture and configured to spatially disperse the photoluminescence wavelength components of the light received through the second aperture.

The system may comprise a first array detector positioned to receive dispersed Raman shifted components and to generate one or more signals indicative of intensity of the dispersed Raman shifted components. The system may comprise a second array detector positioned to receive dispersed photoluminescence components and to generate one or more signals indicative of intensity of the dispersed photoluminescence components.

The system may further comprise a first curved mirror positioned to receive the light from the first aperture and to reflect the light to the first dispersion element and a second curved mirror positioned to receive the light from the second aperture and to reflect the light to the second dispersion element.

The system may comprise a mirror positioned to receive light from the first dispersion element and to reflect the light to the first array detector. The first dispersion element may be a diffraction grating having a first linewidth, and the second dispersion element may be a diffraction grating having the first linewidth, or a second different linewidth.

An optical path length between the first dispersion element and the first array detector may be greater than an optical path length between the second dispersion element and the second array detector.

The system may further comprise at least one of an optical chopper and a pulsed laser to intermittently transmit light to the sample. The system may further comprise a light source configured to generate light of a plurality of wavelengths to intermittently or constantly transmit light to the sample. The system may further comprise a stage configured to position the sample with respect to incoming excitation light. The system may further comprise the sample positioned on the stage.

The system may comprise a filter of a first filter type positioned to filter the light received by the first aperture and a filter of a second filter type positioned to filter the light received by the second aperture. The first filter type may be selected from a notch filter and an edge filter.

These and other features and advantages of the present invention will be more readily apparent from the detailed description of the exemplary implementations set forth below taken in conjunction with the accompanying drawings.

BRIEF DESCRIPTION OF THE DRAWINGS

Like reference symbols in the various drawings indicate like elements.

DETAILED DESCRIPTION

Systems and techniques described herein provide excellent material characterization with an efficient and low cost spectroscopy system.

The systems incorporate detectors configured and positioned to receive light that has interacted with a sample. After interacting with the sample, the light includes a plurality of wavelength components, including photoluminescence components and Raman shifted components. One or more dispersion elements of the system spatially disperse the wavelength components of the light, so that the position in the beam corresponds to the wavelength of the light. A first array detector is positioned to receive the Raman components, so that the Raman spectrum of a particular region of the sample at a particular time can be obtained. A second array detector is positioned to receive the photoluminescence components, so that the PL spectrum for the same region and time can be obtained.

By using array detectors, the intensity as a function of wavelength can be obtained without relative scanning between the detector and the incoming light. Additionally, by enabling contemporaneous Raman and PL spectroscopy, characterization of different regions of the sample is more accurate, because the data does not need to be correlated at a later time. A number of other benefits may be obtained using different embodiments, such as those described below.

Figure 1:
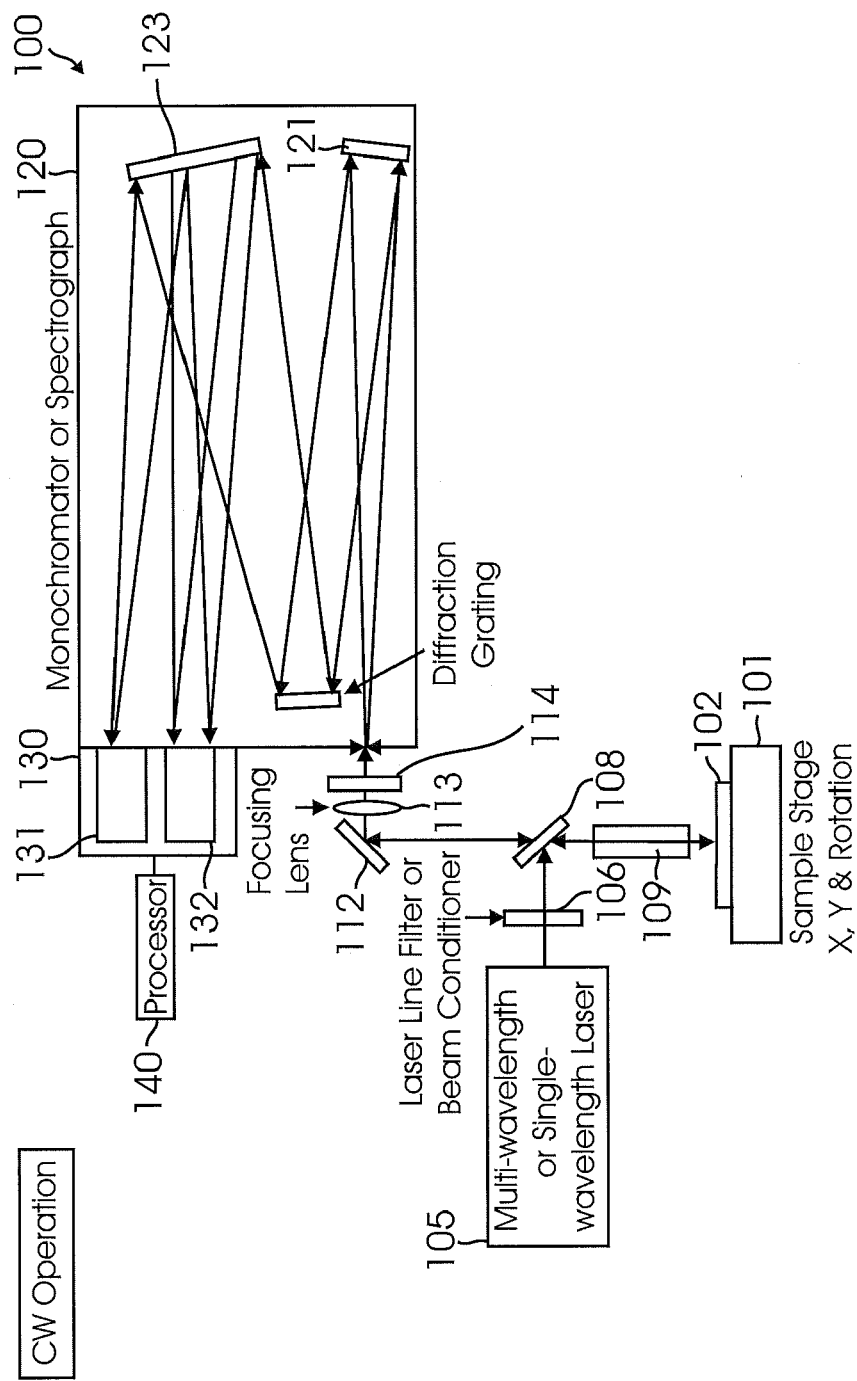
FIG. 1 is a schematic diagram of a spectroscopy system, according to some embodiments.

FIG. 1 illustrates a continuous wave (CW) spectroscopy system 100 that may be used for contemporaneous Raman and photoluminescence (PL) measurement to characterize a sample.

In order to provide information about particular regions of a sample 102, or the entire surface of sample 102, relative motion between incoming excitation light and sample 102 is used. In the example embodiment of FIG. 1, sample 102 is positioned on a stage 101 configured to position sample 102 with respect to incoming light. Stage 101 allows light to be scanned across substantially the entire sample (e.g., in a raster scan pattern), and/or scanned across one or more regions of interest of sample 102. In some embodiments, stage 101 is a sample stage that performs X and Y translation, as well as rotation.

In the embodiment of FIG. 1, incoming excitation light is provided using a light source such as a multi-wavelength or single-wavelength laser source 105. The generated laser light may be modified using a laser line filter or beam conditioner 106.

A half mirror 108 directs light from laser source 105 to sample 102 through an objective lens 109. Incoming light interacts with a portion of sample 102 and light from sample 102 is then transmitted back to half mirror 108. The light from sample 102 may include a number of different wavelength components, as described more fully below.

A portion of the light from sample 102 is transmitted through half mirror 108 and incident on mirror 112. The light may be focused using a focusing lens 113 and filtered using a filter 114 (such as a Raman edge filter, notch filter, or other filter) before being transmitted into a monochromator or spectrograph system 120 through an aperture. Of course many other embodiments are possible; for example, at least some of the optical modification may be performed by elements integrated with system 120. Additional and/or different optical modification may be performed as well (e.g., using filters, lenses, conditioners, blocks, or other optical modification elements).

System 120 spatially disperses light from sample 102 according to wavelength, so that different wavelengths can be discriminated in a detection system 130. In the embodiment illustrated in FIG. 1, system 120 includes one or more curved focusing mirrors 121 that redirect light from sample 102 to a wavelength dispersion mechanism such as a diffraction grating 122.

The dispersed light is incident on a mirror 123 to be directed toward detection system 130. Note that by incorporating one or more mirrors in system 120, the path length of the light is increased to increase the spatial separation of different wavelength components at detection system 130.

In the embodiment of FIG. 1, detection system 130 includes a Raman signal detector 131 and a PL signal detector 132. By providing separate signal detectors for Raman and PL signals, data for each may be obtained at the same time and processed efficiently.

Detectors 131 and 132 may be array detectors such as charge coupled device (CCD) detectors and/or photodiode array detectors. Incorporating array detectors provides an advantage over some prior spectroscopy systems that used detectors that do not discriminate across the area of the detector (like photomultiplier tubes). Using an array detector allows light of a broad range of wavelengths to be detected at once, so that the detector need not be scanned.

Different detector materials may be used for detectors 131 and 132, depending on the circumstances (e.g., the material to be investigated). For example, in order to detect the photoluminescence spectrum of silicon, a silicon detector may be inappropriate, because it cannot generate the needed electron hole pairs. In this case, a non-silicon detector material may be used for detector 132, such as InGaAs (indium gallium arsenide). Similarly, if the material of interest is a wide bandgap material, a silicon detector may be the best choice. Detector 131 may employ the same detector material as detector 132, or they may employ different detector materials.

Detection system 130 is in communication with a processor 140 (which may be separate or at least partially integrated with detection system 130). Processor 140 includes a signal processor to receive signals indicative of the PL signal from detector 132 and signals indicative of the Raman signal from detector 131 and to generate data indicative of the PL signal and the Raman signal. Processor 140 also includes a memory to store data and instructions, and may also include a data processor. The data processor may process the data indicative of the PL signal and the data indicative of the Raman signal to generate spectral information for the PL signal and spectral information for the Raman signal.

Figure 2:
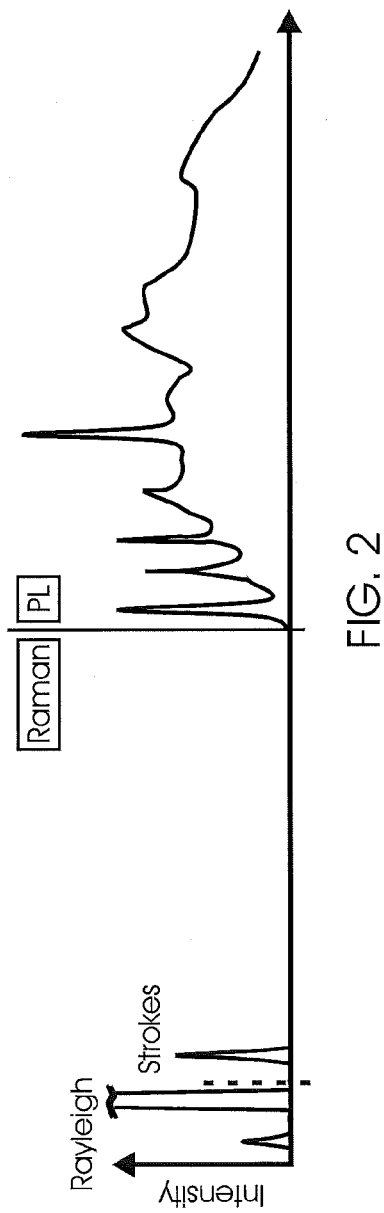
FIG. 2 is a plot of a Raman spectrum and a PL spectrum.

FIG. 2 shows an illustration of Raman and PL signals (in arbitrary intensity units) versus wavelength (in nanometers) that may be obtained using a system such as system 100 of FIG. 1, in CW mode. FIG. 2 illustrates that there is a substantial difference between the spectral characteristics of the Raman and PL signals.

As noted above, in the Raman Effect, monochromatic light at an excitation frequency $v_0$ excites molecules and transforms them into oscillating dipoles. The oscillating dipoles generally emit light of the following three frequencies:

Elastic Rayleigh Scattering: a molecule with no Raman-active modes may absorb a photo with frequency $v_0$. The excited molecule returns to the original basic vibrational state, emitting light with the same frequency as the absorbed photon ($v_0$). The majority of incident photons in spontaneous Raman undergo elastic Rayleigh scattering (about 99.999%).

Stokes Raman scattering: A photon with frequency $v_0$ is absorbed by a Raman-active molecule which at the time of interaction is in the basic vibrational state. Part of the photon's energy is transferred to the Raman-active mode with frequency $v_m$ and the resulting frequency of scattered light is reduced to $v_0-v_m$.

Anti-Stokes Raman scattering: A photon with frequency $v_0$ is absorbed by a Raman-active molecule which at the time of interaction is in the excited vibrational state. Excessive energy of an excited Raman-active mode is released, the molecule returns to the basic vibrational state, and the resulting frequency of scattered light is increase to $v_0+v_m$. Herein, the phrase "Raman signal" refers to the Stokes signal, the anti-Stokes signal, or both.

Detection of the Raman signal may be quite difficult. Most of the incident photons undergo elastic Rayleigh scattering, so that the intensity of the Rayleigh scattered light is much greater than the intensity of the Raman signal(s) (Stokes and/or anti-Stokes). Additionally, the difference in wavelength between the Raman signal and the Rayleigh signal is quite small. In order to detect the Raman signal with sufficient resolution to accurately determine factors such as the change in frequency, intensity, and full width at half maximum (FWHM), noise due to the Rayleigh signal needs to be reduced or eliminated.

A number of different techniques may be used to reduce the effect of Rayleigh scattering on detection of the Stokes and anti-Stokes scattered light. One technique is to increase the focal length of the spectrograph, so that the spatial separation between the Rayleigh and Stokes wavelengths is large enough that the Rayleigh signal can be effectively blocked. For a particular probe wavelength and spectrograph configuration, the spatial position of the Rayleigh peak can be determined at one or more locations in spectrograph 120, and a block positioned to substantially prevent the Rayleigh scattered light from being detected. In some embodiments, a block may be positioned close to detector 131, where the spatial separation between the Rayleigh and Raman signals is greatest.

Another technique is to use one or more filters to substantially remove the Rayleigh signal from the light. For example, notch filters, tunable filters, edge filters, or other filters may be used. In embodiments in which an edge filter is used, the anti-Stokes signal is filtered along with the Rayleigh signal. However, many applications use only the Stokes component of the Raman signal.

Another challenge in Raman spectroscopy is the relative narrowness of the Raman peak. In order to adequately characterize the Raman signal, the Raman detector and spectrograph should be configured so that the intensity profile can be determined to the accuracy needed for the application. Some techniques that may be used to enhance detection of the Raman signal include increasing the focal length of the spectrograph and increasing the wavelength dispersion of the Raman components.

As noted above, photoluminescence refers to the optical emission obtained by photon excitation. The energy from the incoming light causes an electronic transition of one or more electrons in the material from a lower energy state to a higher energy state. The material emits light as a result of the electron transitioning from the higher energy state to a lower energy state. The spectral signature obtained from detecting the light provides information about material components and the like.

The photoluminescence signal poses a different challenge than the Raman signal. As FIG. 2 illustrates, the wavelength range encompassing different peaks is relatively large for the photoluminescence signal, so that the PL detector and spectrograph should be positioned and configured to capture signals from the different wavelengths of interest.

Figure 6:
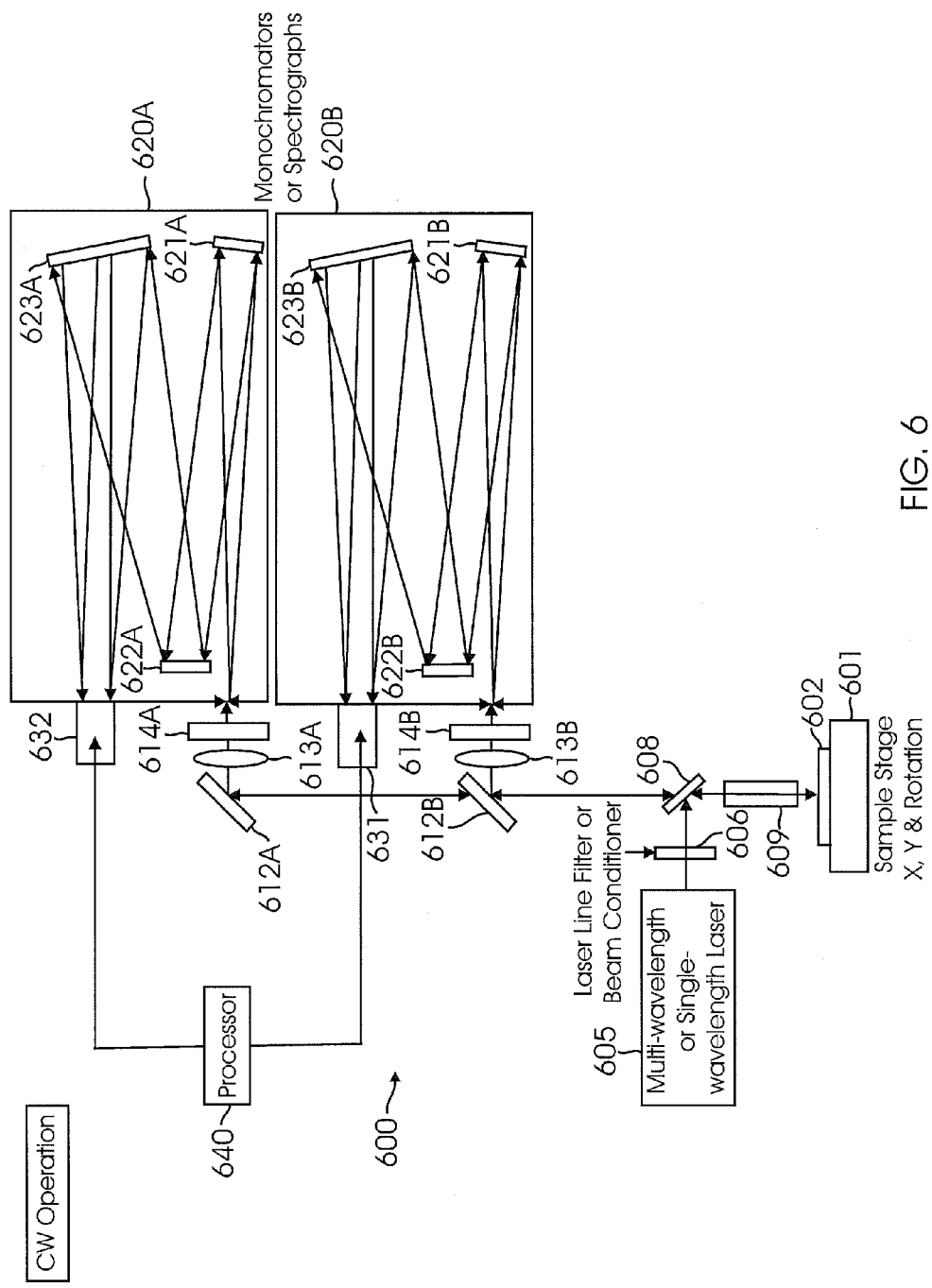
FIG. 6 is a schematic diagram of a spectroscopy system, according to some embodiments.

Although some prior systems allow for Raman and PL spectroscopy, the current systems and techniques offer enhanced efficiency, as well as better signal to noise ratios for the obtained spectral information. These benefits may be obtained using an integrated monochromator or spectrograph (such as spectrograph 120 of FIG. 1) and differentiated detection elements (such as detectors 131 and 132 of detection system 130 of FIG. 1), or by using differentiated spectrographs and detection systems (e.g., as shown in FIG. 6 and described below).

Figure 3A:
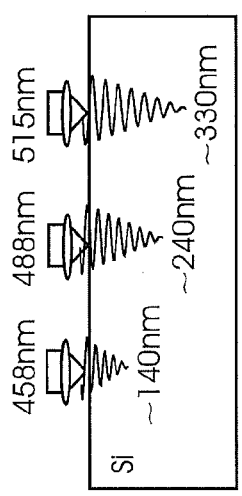
FIG. 3A illustrates the penetration depth of three different excitation wavelengths.

Additional benefits may be obtained by performing spectrometry when laser source 105 generates light with multiple wavelengths, using one or more lasers. FIG. 3A illustrates the effect on light penetration depth on wavelength for a silicon sample. Light with a wavelength of 458 nanometers penetrates the sample to about 140 nanometers, while 488 nanometer light penetrates to about 240 nanometers. 515 nanometer light penetrates to a depth of about 330 nanometers. Thus, in order to characterize a material as a function of depth, an appropriate excitation (probing) wavelength may be selected.

Figure 3B:
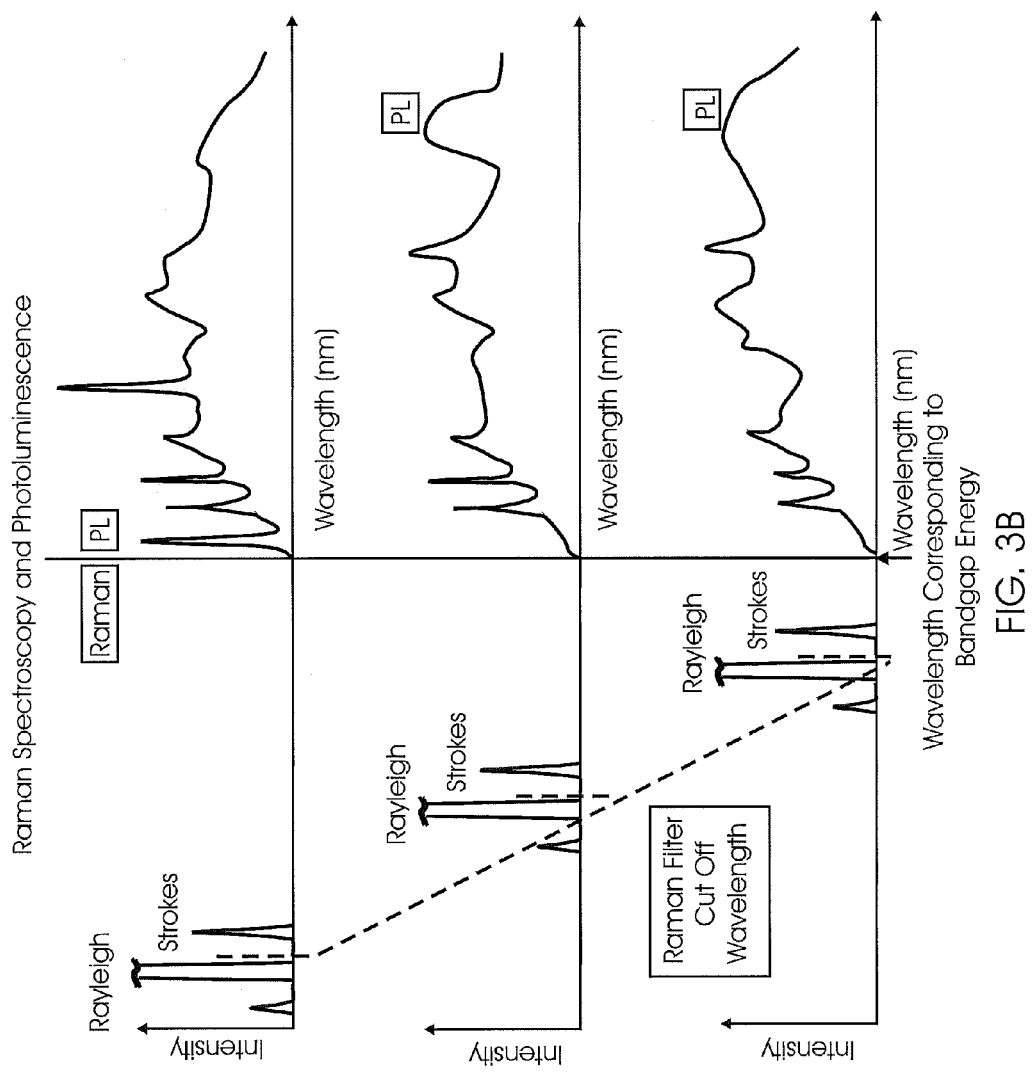
FIG. 3B is a plot of a Raman spectrum and a PL spectrum for each of the three excitation wavelengths of FIG. 3A.

FIG. 3B shows calculated intensity versus wavelength plots for the Raman and PL signals at three different wavelengths. The PL signal changes to reflect the integrated signal from the different depths probed by the different excitation wavelengths. The Raman signals shift with different excitation wavelengths, and obtain information about material properties as a function of depth.

Figure 4A:
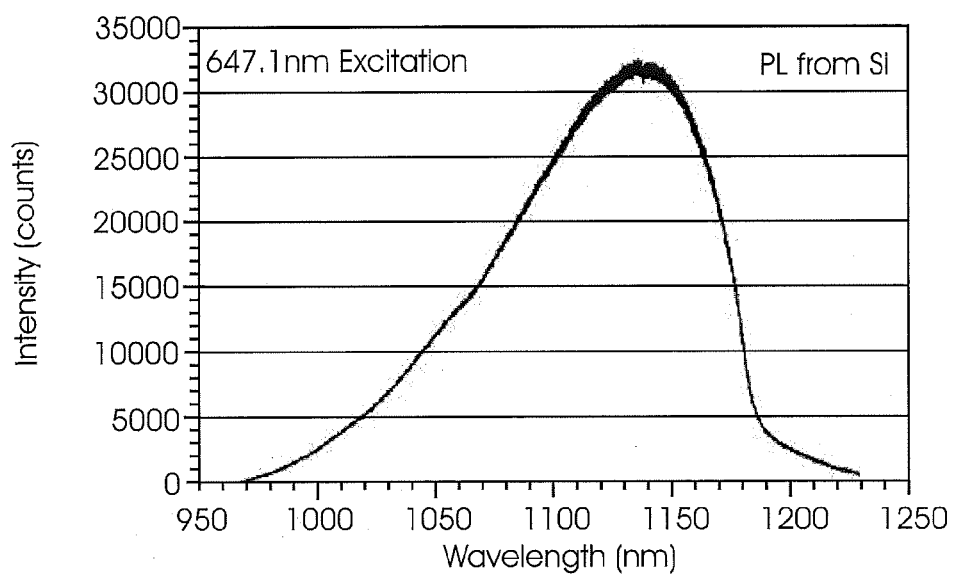
FIG. 4A is a plot of a measured PL spectrum for four different excitation wavelengths.
Figure 4B:
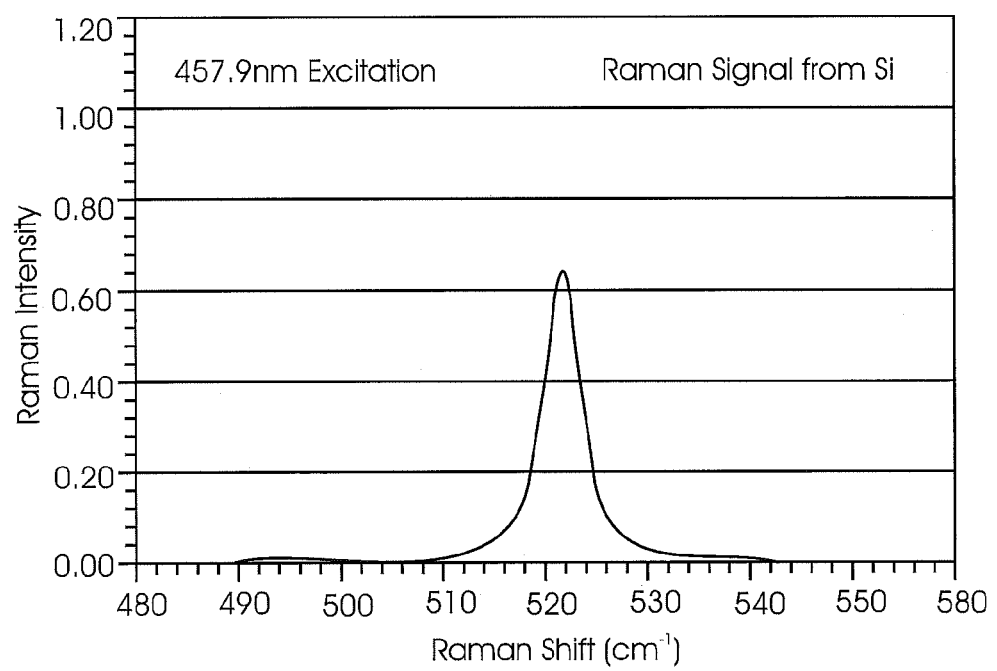
FIGS. 4B to 4E are plots of measured Raman spectra for four different excitation wavelengths.
Figure 4C:
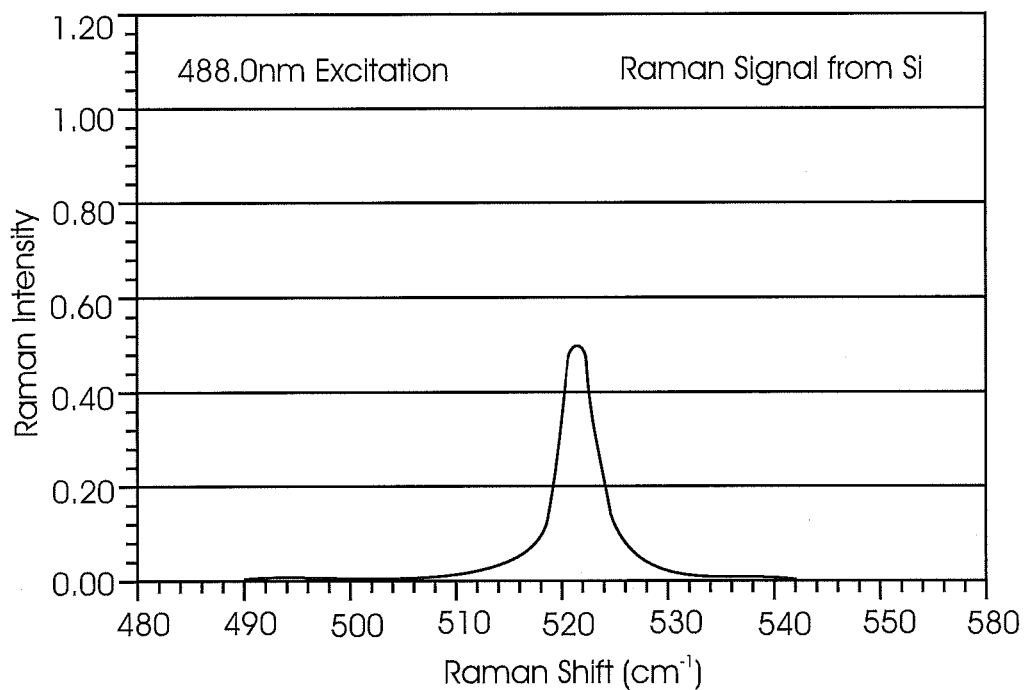
Figure 4D:
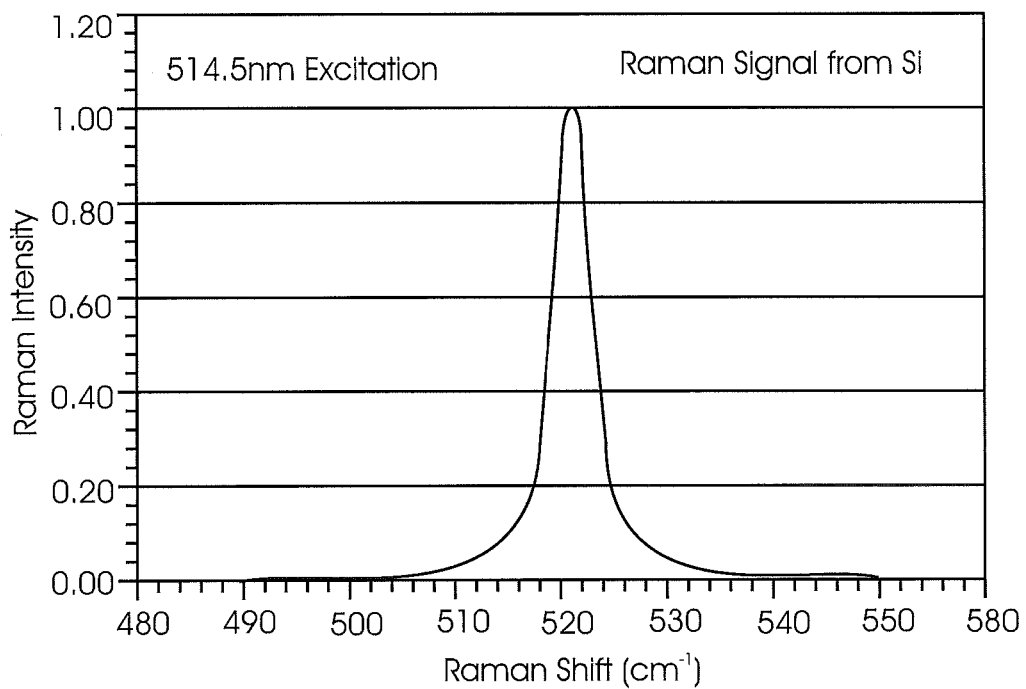
Figure 4E:
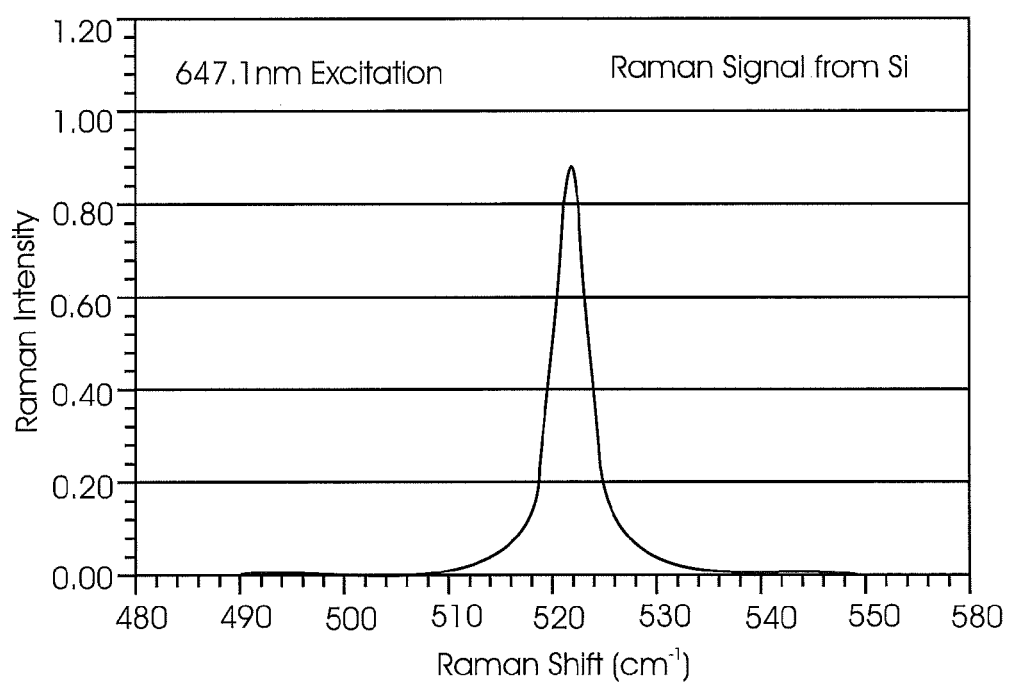

FIGS. 4A to 4E show experimentally obtained PL and Raman spectra for four different excitation wavelengths: 457.9 nm, 488.0 nm, 514.5 nm, and 647.1 nm. As FIG. 4A shows, the overall effect of wavelength on the PL spectrum for the sample being characterized is relatively small. However, FIGS. 4B to 4E show that the shape and height of the Raman peak changes significantly for the sample. For example, the peak height of the 514.5 nm excitation wavelength is approximately twice the peak height of the 488.0 nm excitation wavelength depending on inhomogeneity of crystal (or material) quality of sample in the depth direction. For more homogeneous materials, the difference between Raman signals for different excitation wavelengths would be less.

Figure 5:
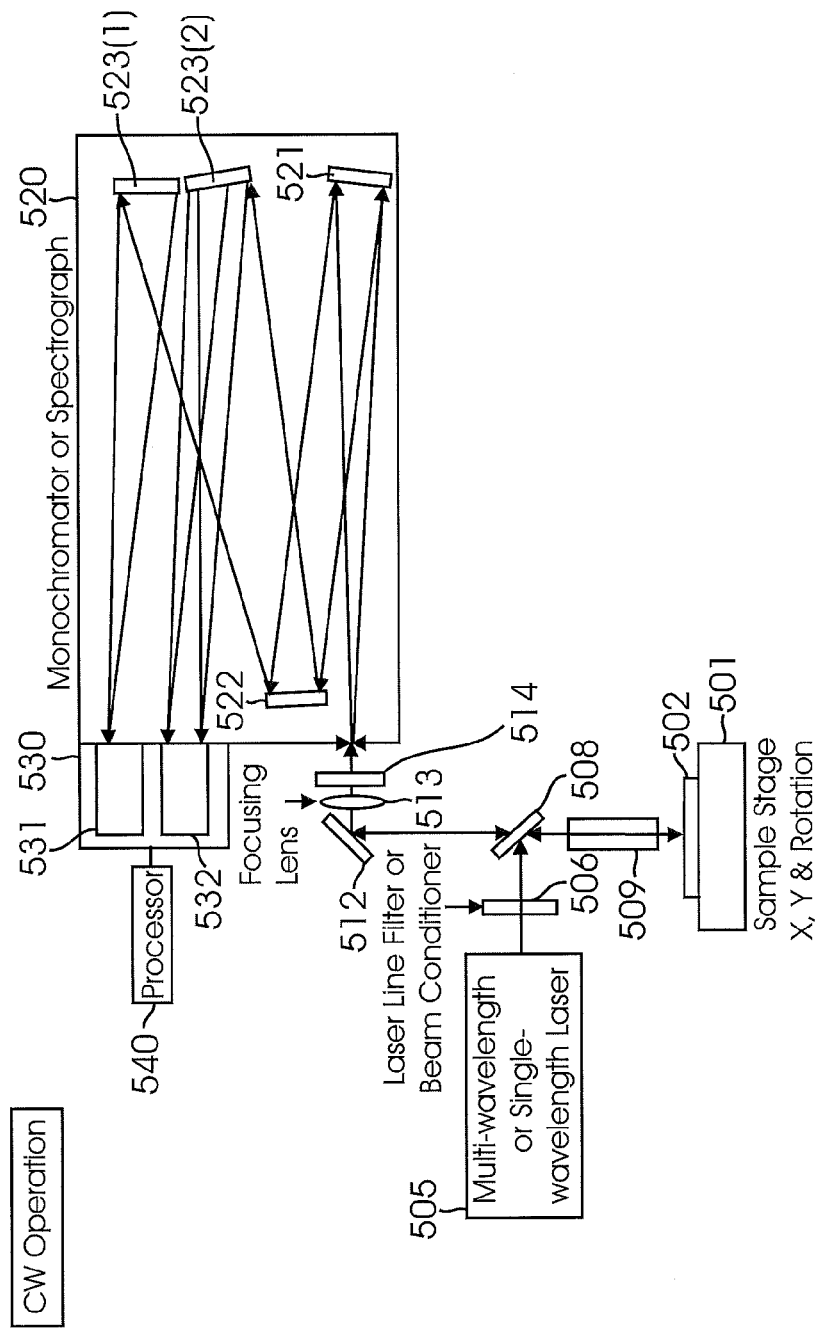
FIG. 5 is a schematic diagram of a spectroscopy system, according to some embodiments.

Many different embodiments may be used, incorporating one or more different or additional elements (or omitting one or more elements). FIG. 5 shows another embodiment of a continuous wave (CW) spectroscopy system 500 that may be used for contemporaneous Raman and photoluminescence (PL) measurement.

In FIG. 5, spectrograph 520 integrates optics to modify light from a sample 502 containing both PL and Raman scattered components. However, rather than a single focusing mirror such as mirror 123 of FIG. 1, spectrograph 520 includes separate (divided) focusing mirrors 523(1) and 523(2). In the embodiment of FIG. 5, focusing mirror 523(1) directs PL light to PL signal detector 531, while focusing mirror 523(2) directs Raman scattered light to Raman signal detector 532.

The embodiment of FIG. 5 may allow for better differentiation between PL and Raman signals, enhancing the user's ability to determine one or more material properties of sample 502. Although mirrors 523(1) and 523(2) are shown as the same, and shown being positioned at similar distances from detectors 531 and 532, they need not be. The design and positioning of mirrors 523(1) and 523(2) may be selected based on the material being probed, the wavelength(s) of light used, the configuration and positioning of the detectors used, or other parameter.

Additionally, one or more elements of system 520 (or other spectroscopy system embodiments) may be moveable. For example, diffraction grating 522 may be rotatable, so that the focus of the signals may be optimized. Additionally (or instead), either or both of mirrors 523(1) and 523(2) may be moveable to accommodate the particular spectroscopy application.

The integrated spectrograph in the above-described embodiments allow for cost- and space-efficient spectroscopy. However, for some applications, differentiated spectrographs (systems in which wavelength dispersion for the PL and Raman signals is performed at least partially in different spectrograph sub-systems) may be preferred. For example, for an application in which the sample is a silicon sample, the difference in wavelengths of interest for the Raman spectrum and the PL system may be great enough that separate spectrographs may provide a substantial benefit. The bandgap of silicon is about 1.1 eV, so that the photoluminescence wavelengths of interest are in the infrared region of the spectrum (about 1 micron to about 1.4 microns). That is, both the wavelength and the wavelength range for the photoluminescence signal are relatively large. By contrast, Raman scattered light has a wavelength very close to the wavelength of the excitation light, and extends over a narrow wavelength range.

FIG. 6 shows an embodiment of a continuous wave (CW) spectroscopy system 600 that may be used for contemporaneous Raman and photoluminescence (PL) measurement that incorporates differentiated spectrographs.

In system 600, light from a sample 602 is transmitted through a half mirror 608. It is then incident on a low pass filter or mirror 612B. Some of the incident light is transmitted through filter or mirror 612B to mirror 612A. Light reflected from mirror 612A passes through a lens 613A and a filter such as low pass filter 614A and into spectrograph 620A through an aperture. Additionally, some of the incident light is transmitted through lens 613B and Raman edge filter 614B into monochromator or spectrograph 620B.

In spectrograph 620A, light is reflected from a curved focusing mirror 621A to a dispersion element 622A such as a diffraction grating. The light from dispersion element 622A is reflected to a PL signal detector 632 using a focusing mirror 623A.

In spectrograph 620B, light is reflected from a curved focusing mirror 621B to a dispersion element 622B such as a diffraction grating. The light from dispersion element 622B is reflected to a Raman signal detector 631 using a focusing mirror 623B.

The embodiment of FIG. 6 may provide a number of benefits. First, spectrographs 620A and 620B may be tailored for the particular spectroscopy being performed.

For example, for the Raman signal, a high line density (e.g., 1200 mm$^{-1}$) diffraction grating may be used as dispersion element 622B. However, a lower line density grating (e.g., 300 mm$^{-1}$ or 600 mm$^{-1}$) may be appropriate as dispersion element 622A. Additionally, the type of detector, position of detector, types of elements, and positions of the elements may be selected for improved detection of the PL or Raman signal.

The current inventor recognized that time-resolved spectroscopy may provide a number of additional benefits. Therefore, in some embodiments, the light source may be a pulsed light source. That is, a pulsed laser and/or optical chopper may be used so that light is incident on the sample intermittently rather than continuously.

Traces of peak positions and the areas between light pulses provides information on: material homogeneity, composition, and stress (Raman signal), as well as electron-hole recombination processes (paths) and recombination mechanisms for the sample, dopant energy level(s) dopant species, dopant concentration, defects levels, defect types, material quality, and optical properties (PL signal).

Figure 7:
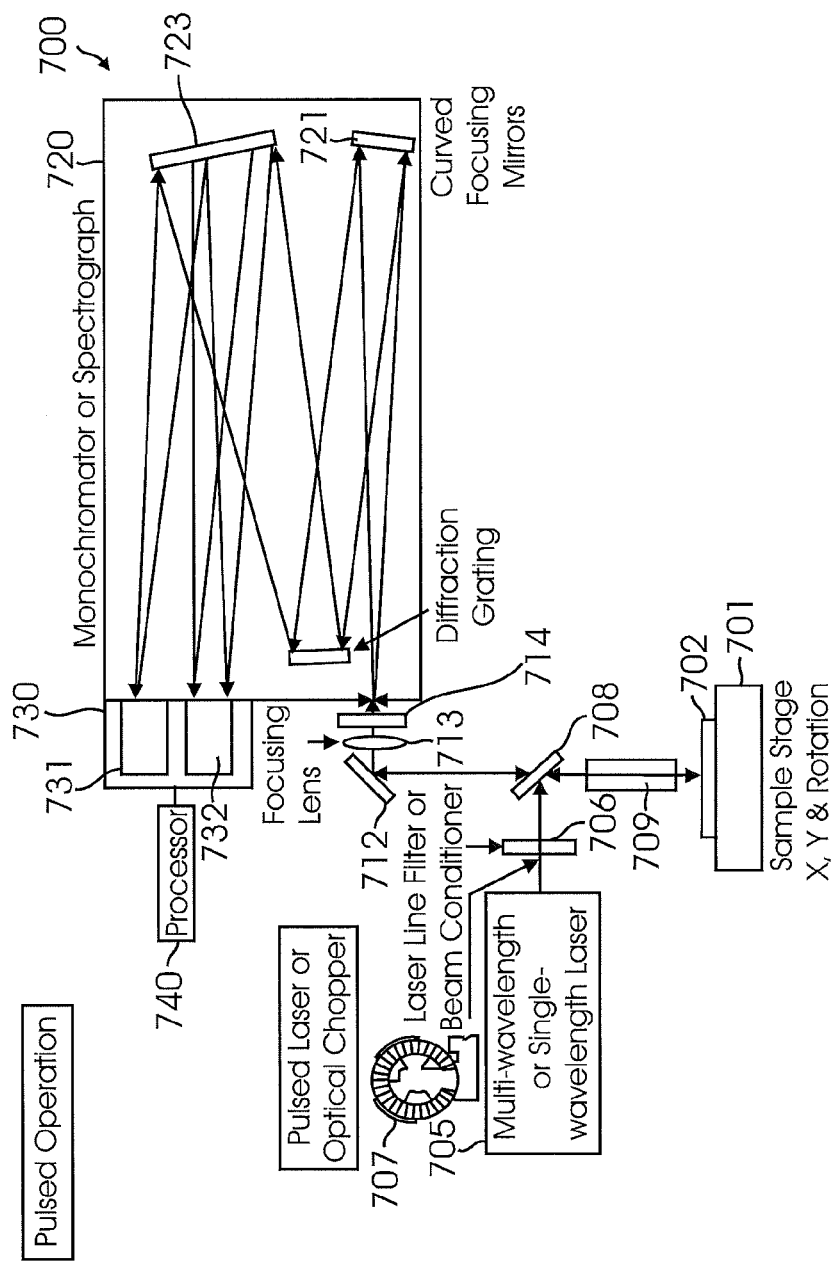
FIG. 7 is a is a schematic diagram of a spectroscopy system, according to some embodiments.

FIG. 7 shows an embodiment of a system 700 to perform pulsed PL and Raman spectroscopy. In the embodiment of FIG. 7, an optical chopper 707 is positioned in the optical path of light from laser source 705. As a result, pulsed light is incident on surface 702, and generates Raman and PL signal pulses. The Raman and PL signals are separated in spectrograph 720, and detected in detection system 730.

Detection system 730 is in communication with a processor 740 (which may be separate or at least partially integrated with detection system 730). Processor 740 includes a signal processor to receive signals indicative of the PL signal from detector 732 and signals indicative of the Raman signal from detector 731 and to generate data indicative of the PL signal and the Raman signal. Processor 740 also includes a memory to store data and instructions, and may also include a data processor. The data processor may process the data indicative of the PL signal and the data indicative of the Raman signal to generate time-resolved spectral information for the PL signal and time-resolved spectral information for the Raman signal.

Figure 8A:
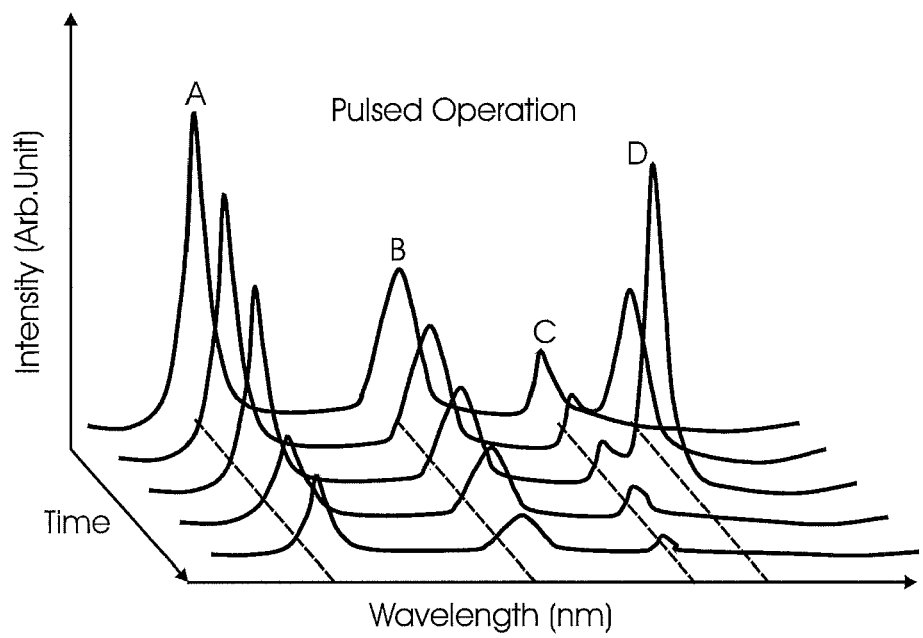
FIGS. 8A and 8B are plots of intensity versus time for four different PL peaks illustrating time-resolved spectroscopy.
Figure 8B:
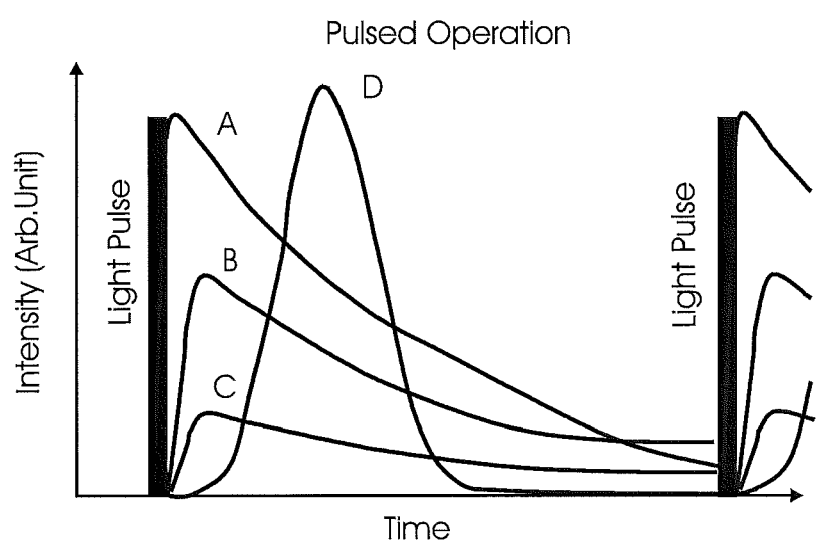

FIGS. 8A and 8B show the photoluminescence signal that may be obtained using a time resolved system such as system 700 of FIG. 7. FIGS. 8A and 8B show that, over time, the peak height for a particular line changes, and the difference between different peak heights changes as well. Thus, measuring the PL system over time provides information about the energy levels and transition rates for different states.

Figure 9:
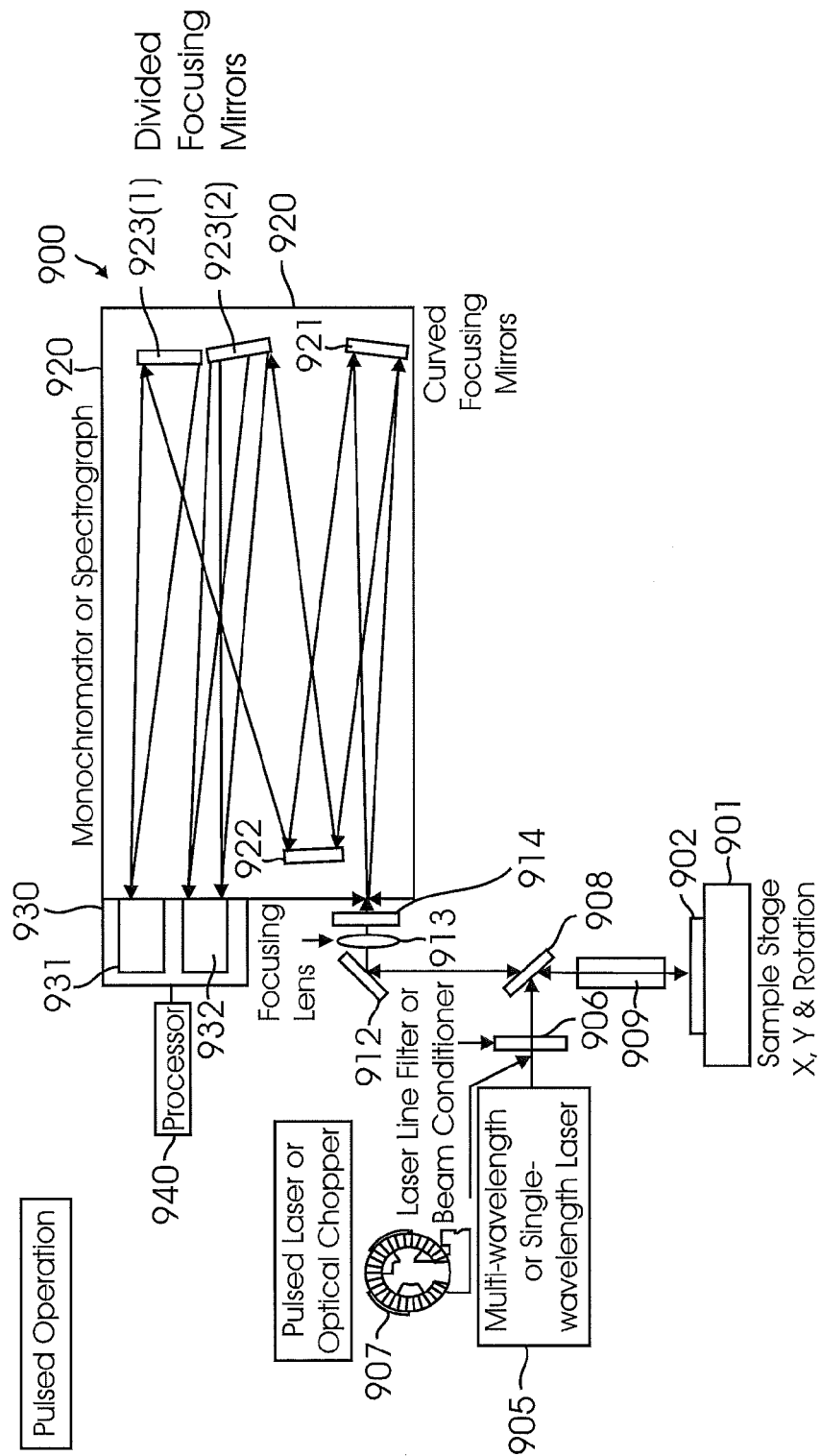
FIG. 9 is a schematic diagram of a spectroscopy system, according to some embodiments.
Figure 10:
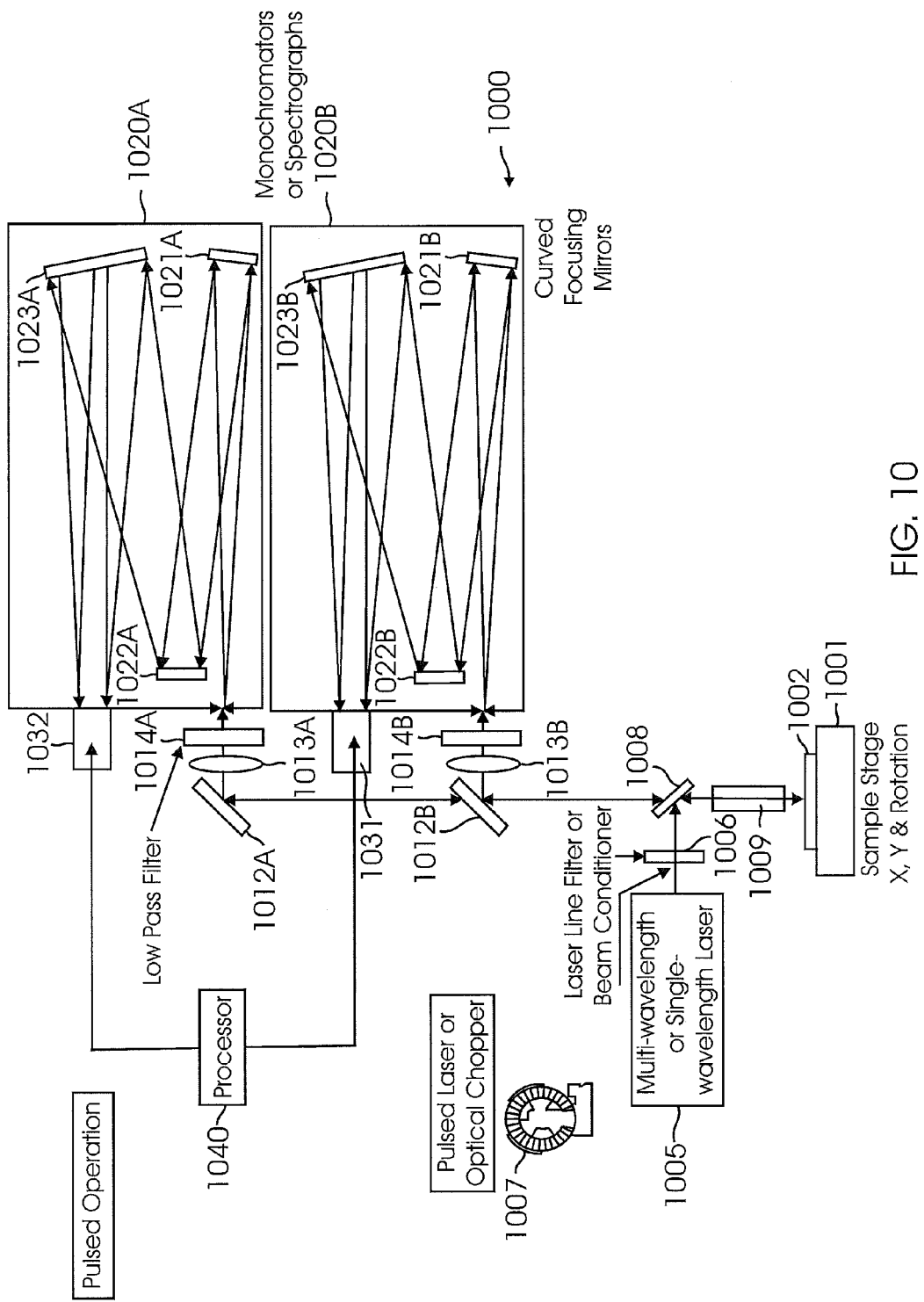
FIG. 10 is a schematic diagram of a spectroscopy system, according to some embodiments.

Time resolved spectrometry may be implemented with other embodiments of combined PL and Raman spectroscopy systems. FIG. 9 shows a system 900 configured to do time resolved spectroscopy and incorporating divided focusing mirrors 923(1) and 923(2). FIG. 10 shows a system 1000 configured to do time resolved spectroscopy and incorporating differentiated spectrographs 1020A and 1020B.

In implementations, the above described techniques and their variations may be implemented at least partially as computer software instructions. Such instructions may be stored on one or more machine-readable storage media or devices and are executed by, e.g., one or more computer processors, or cause the machine, to perform the described functions and operations.

A number of implementations have been described. Although only a few implementations have been disclosed in detail above, other modifications are possible, and this disclosure is intended to cover all such modifications, and most particularly, any modification which might be predictable to a person having ordinary skill in the art. For example, different or additional optical elements may be used (or elements may in some cases by omitted). Many alternatives are known to persons of ordinary skill in the art. We also note that the word "light" used herein does not denote any particular portion of the electromagnetic spectrum. E.g., the phrase "visible light" refers to light in the visible spectrum, while "light" can refer to visible light, infrared light, or light in other wavelength ranges.

Also, only those claims which use the word "means" are intended to be interpreted under 35 USC 112, sixth paragraph. In the claims, the word "a" or "an" embraces configurations with one or more element, while the phrase "a single" embraces configurations with only one element, notwithstanding the use of phrases such as "at least one of" elsewhere in the claims. Moreover, no limitations from the specification are intended to be read into any claims, unless those limitations are expressly included in the claims. Accordingly, other embodiments are within the scope of the following claims.

What is claimed is:

1. A spectroscopy system comprising:
    an aperture positioned to receive light from a sample, the light including a plurality of wavelength components including photoluminescence wavelength components and Raman shifted components;
    a dispersion element positioned in the optical path of the light and configured to spatially disperse the wavelength components of the light;
    a first array detector positioned to receive Raman shifted components and to generate one or more signals indicative of intensity of the Raman shifted components; and
    a second array detector positioned to receive photoluminescence components and to generate one or more signals indicative of intensity of the photoluminescence components.

2. The system of claim 1, further comprising a curved mirror positioned to receive the light from the aperture and to reflect the light to the dispersion element.

3. The system of claim 2, further comprising a mirror positioned to receive light from the dispersion element and to reflect the light to the first array detector and the second detector.

4. The system of claim 2, further comprising:
    a first mirror positioned to receive light from the dispersion element and to reflect the light to the first array detector; and
    a second mirror positioned to receive light from the dispersion element and to reflect the light to the second array detector.

5. The system of claim 1, wherein the first array detector comprises a first detector material, and wherein the second array detector comprises a second different detector material.

6. The system of claim 1, wherein the first detector material comprises silicon, and wherein the second different detector material comprises a material with a bandgap larger than one electron volt.

7. The system of claim 1, further comprising at least one of an optical chopper and a pulsed laser to intermittently transmit light to the sample.

8. The system of claim 1, further comprising a light source configured to generate light of a plurality of wavelengths to intermittently or constantly transmit light to the sample.

9. The system of claim 1, further comprising a stage configured to position the sample with respect to incoming excitation light.

10. A spectroscopy system comprising:
    a first aperture positioned to receive light from a region of a sample at a particular time, the light including a plurality of wavelength components including Raman wavelength components;
    a second aperture positioned to receive light from the region of the sample at the particular time, the light including a plurality of wavelength components including photoluminescence shifted components;
    a first dispersion element positioned in the optical path of the light received through the first aperture and configured to spatially disperse the Raman wavelength components of the light received through the first aperture;
    a second dispersion element positioned in the optical path of the light received through the second aperture and configured to spatially disperse the photoluminescence wavelength components of the light received through the second aperture;
    a first array detector positioned to receive dispersed Raman shifted components and to generate one or more signals indicative of intensity of the dispersed Raman shifted components; and
    a second array detector positioned to receive dispersed photoluminescence components and to generate one or more signals indicative of intensity of the dispersed photoluminescence components.

11. The system of claim 10, further comprising:
a first curved mirror positioned to receive the light from the first aperture and to reflect the light to the first dispersion element; and
a second curved mirror positioned to receive the light from the second aperture and to reflect the light to the second dispersion element.

12. The system of claim 11, further comprising a mirror positioned to receive light from the first dispersion element and to reflect the light to the first array detector.

13. The system of claim 10, wherein the first dispersion element is a diffraction grating having a first linewidth, and wherein the second dispersion element is a diffraction grating have a second different linewidth.

14. The system of claim 10, wherein an optical path length between the first dispersion element and the first array detector is greater than an optical path length between the second dispersion element and the second array detector.

15. The system of claim 1, further comprising at least one of an optical chopper and a pulsed laser to intermittently transmit light to the sample.

16. The system of claim 10, further comprising a light source configured to generate light of a plurality of wavelengths to intermittently or constantly transmit light to the sample.

17. The system of claim 10, further comprising a stage configured to position the sample with respect to incoming excitation light.

18. The system of claim 17, further comprising the sample positioned on the stage.

19. The system of claim 10, further comprising:
a filter of a first filter type positioned to filter the light received by the first aperture; and
a filter of a second filter type positioned to filter the light received by the second aperture.

20. The system of claim 19, wherein the first filter type is selected from a notch filter and an edge filter.

* * * * *